(12) United States Patent
Wang et al.

(10) Patent No.: US 11,096,628 B2
(45) Date of Patent: Aug. 24, 2021

(54) HEART RATE DETECTION METHOD AND APPARATUS, AND ELECTRONIC TERMINAL THEREOF

(71) Applicant: SHENZHEN GOODIX TECHNOLOGY CO., LTD., Shenzhen (CN)

(72) Inventors: Xinshan Wang, Shenzhen (CN); Guoliang Li, Shenzhen (CN); Ke Yang, Shenzhen (CN); Duan Zeng, Shenzhen (CN)

(73) Assignee: SHENZHEN GOODIX TECHNOLOGY CO., LTD., Shenzhen (CN)

( * ) Notice: Subject to any disclaimer, the term of this patent is extended or adjusted under 35 U.S.C. 154(b) by 461 days.

(21) Appl. No.: 16/164,800

(22) Filed: Oct. 19, 2018

(65) Prior Publication Data

US 2019/0059822 A1  Feb. 28, 2019

Related U.S. Application Data

(63) Continuation of application No. PCT/CN2017/098531, filed on Aug. 22, 2017.

(51) Int. Cl.
*A61B 5/00* (2006.01)
*A61B 5/024* (2006.01)
(Continued)

(52) U.S. Cl.
CPC ........... *A61B 5/7207* (2013.01); *A61B 5/024* (2013.01); *A61B 5/02416* (2013.01);
(Continued)

(58) Field of Classification Search
CPC .... A61B 5/2707; A61B 5/024; A61B 5/02416
See application file for complete search history.

(56) References Cited

U.S. PATENT DOCUMENTS

| 2010/0268093 A1 | 10/2010 | Balji et al. |
| 2014/0323874 A1 | 10/2014 | Addison et al. |
| (Continued) | | |

FOREIGN PATENT DOCUMENTS

| CN | 02048558 A | 5/2011 |
| CN | 102048558 A | 5/2011 |
| (Continued) | | |

OTHER PUBLICATIONS

Gan,Yiming, "Measurement of Pulse Signals by Wearable Pressure Sensor", Jan. 15, 2008. 84 Pages.

*Primary Examiner* — Son T Le
*Assistant Examiner* — Nana Owusu Ansah
(74) *Attorney, Agent, or Firm* — Brion Raffoul (57) ABSTRACT

A heart rate detection method includes: acquiring a plurality of time-domain heart rate detection data; if the time-domain heart rate detection data includes a weak interference signal, extracting a first feature point from the time-domain heart rate detection data, and collecting statistics on feature data of the first feature point to determine time-domain heart rate detection data used in calculating heart rate; if the time-domain heart rate detection data includes a strong interference signal, transforming the time-domain heart rate detection data to a frequency domain to obtain a plurality of frequency-domain heart rate detection data, extracting a second feature point from the frequency-domain heart rate detection data, and collecting statistics on feature data of the second feature point to determine frequency-domain heart rate detection data used in calculating heart rate; and calculating the heart rate based on the time-domain or the frequency-domain heart rate detection data.

17 Claims, 5 Drawing Sheets

(51) Int. Cl.
 *A61B 5/11* (2006.01)
 *G06K 9/00* (2006.01)
(52) U.S. Cl.
 CPC ............ *A61B 5/1102* (2013.01); *A61B 5/721* (2013.01); *A61B 5/7235* (2013.01); *G06K 9/0053* (2013.01); *A61B 5/7221* (2013.01); *A61B 5/7253* (2013.01); *A61B 2562/0219* (2013.01)

(56) References Cited

U.S. PATENT DOCUMENTS

| | | | |
|---|---|---|---|
| 2015/0313549 A1 | 11/2015 | Lee et al. | |
| 2016/0051158 A1 | 2/2016 | Silva | |
| 2018/0116597 A1* | 5/2018 | Yu | A61B 5/0245 |

FOREIGN PATENT DOCUMENTS

| | | | | |
|---|---|---|---|---|
| CN | 104887215 A | 9/2015 | | |
| CN | 104994780 | 10/2015 | | |
| CN | 105796096 A | 7/2016 | | |
| CN | 105816163 A | 8/2016 | | |
| CN | 105943012 | 9/2016 | | |
| CN | 106606358 | 5/2017 | | |
| CN | 106667474 | 5/2017 | | |
| CN | 105816163 B * | 3/2019 | ......... A61B 5/02416 |
| EP | 3181038 A1 * | 6/2017 | ......... A61B 5/02433 |
| EP | 3181038 A1 | 6/2017 | | |

* cited by examiner

HEART RATE DETECTION METHOD AND APPARATUS, AND ELECTRONIC TERMINAL THEREOF

CROSS-REFERENCE TO RELATED APPLICATIONS

The present application is a continuation of international application No. PCT/CN2017/098531, filed on Aug. 22, 2017, which is hereby incorporated by reference in its entireties

TECHNICAL FIELD

Embodiments of the present application relate to the technical field of biological feature detection, and in particular, relate to a heart rate detection method and apparatus, and an electronic terminal thereof.

BACKGROUND

In recent years, with the continuous development of people's life, people are more and more placing more concerns on health, and it is an effective to build the health by sports or exercise. During the sports and exercise, the heart rate is an important indicator reflecting the motion state of the human body, and an accurate heart rate is capable of truly reflecting the motion state of the human body.

However, since heart rate measurement is mostly commonly based on photoplethysmograph (PPG), when the human body is in a motion state, heart rate detection data (that is, a PPG signal) is easily subject to interference by the motion. For example, in the motion state, since shift occurs between the skin and the measurement device (for example, an electronic terminal equipped with a heart rate detection function), causing a light propagation path changes. Therefore, some motion interference signals or the like may be superimposed in addition to the pulse signal of the human body in the heart rate detection signal. As a result, the accuracy of the detected heart rate is low.

SUMMARY

In view of the above, one technical problem to be solved by embodiments of the present application is to provide a heart rate detection method and apparatus, and an electronic terminal, to address the above technical defects in the prior art.

Embodiments of the present application provide a heart rate detection method. The method includes:

acquiring a plurality of time-domain heart rate detection data;

if the plurality of time-domain heart rate detection data includes a weak interference signal, extracting a first feature point from the plurality of time-domain heart rate detection data, and collecting statistics on feature data of the first feature point to determine time-domain heart rate detection data used in calculating heart rate;

if the plurality of time-domain heart rate detection data includes a strong interference signal, transforming the plurality of time-domain heart rate detection data to a frequency domain to obtain a plurality of frequency-domain heart rate detection data, extracting a second feature point from the plurality of frequency-domain heart rate detection data, and collecting statistics on feature data of the second feature point to determine frequency-domain heart rate detection data used in calculating heart rate; and calculating the heart rate according to the time-domain heart rate detection data or the frequency-domain heart rate detection data used in calculating heart rate.

Embodiments of the present application provide a heart rate detection apparatus. The apparatus includes:

an acquiring module, configured to acquire a plurality of time-domain heart rate detection data;

a time-domain module, configured to: if the plurality of time-domain heart rate detection data include a weak interference signal, extract a first feature point from the plurality of time-domain heart rate detection data, and collect statistics on feature data of the first feature point to determine time-domain heart rate detection data involved heart rate calculation;

a frequency-domain module, configured to: if the plurality of time-domain heart rate detection data includes a strong interference signal, transform the plurality of time-domain heart rate detection data to a frequency domain to obtain a plurality of frequency-domain heart rate detection data, extract a second feature point from the plurality of frequency-domain heart rate detection data, and collect statistics on feature data of the second feature point to determine frequency-domain heart rate detection data used in calculating heart rate; and a calculating module, configured to calculate the heart rate according to the time-domain heart rate detection data or the frequency-domain heart rate detection data used in calculating heart rate.

Embodiments of the present application further provide an electronic terminal. The electronic terminal includes the above heart rate detection apparatus.

In the above technical solutions according to the present application, a plurality of time-domain heart rate detection data is firstly acquired; if the plurality of time-domain heart rate detection data includes a weak interference signal, a first feature point in the plurality of time-domain heart rate detection data is acquired, and statistics on feature data of the first feature point are collected to determine time-domain heart rate detection data used in calculating heart rate; if the plurality of time-domain heart rate detection data includes a strong interference signal, the plurality of time-domain heart rate detection data is transformed to a frequency domain to obtain a plurality of frequency-domain heart rate detection data, a second feature point is extracted from the plurality of frequency-domain heart rate detection data, and statistics are collected on feature data of the second feature point to determine frequency-domain heart rate detection data used in calculating heart rate; and the heart rate is calculated according to the time-domain heart rate detection data or the frequency-domain heart rate detection data used in calculating heart rate. In this way, the accuracy of the detected heart rate is improved.

BRIEF DESCRIPTION OF THE DRAWINGS

To describe technical solutions according to the embodiments of the present application or in the related art, drawings that are to be referred for description of the embodiments or the related art are briefly described hereinafter. Apparently, the drawings described hereinafter merely illustrate some embodiments of the present application. Persons of ordinary skill in the art may also derive other drawings based on the drawings described herein.

DETAILED DESCRIPTION

Nevertheless, it is not necessary to require that any technical solution according to the embodiments of the present application achieves all of the above technical effects.

To make a person skilled in the art better understand the technical solutions of the embodiments of the present application, the technical solutions of the present application are clearly and completely described with reference to the accompanying drawings of the embodiments of the present application. Apparently, the described embodiments are only a part of the embodiments of the present application, rather than the entire embodiments. Based on the embodiments of the present application, all other embodiments derived by persons of ordinary skill in the art without any creative efforts shall fall within the protection scope of the present application.

Figure 1:
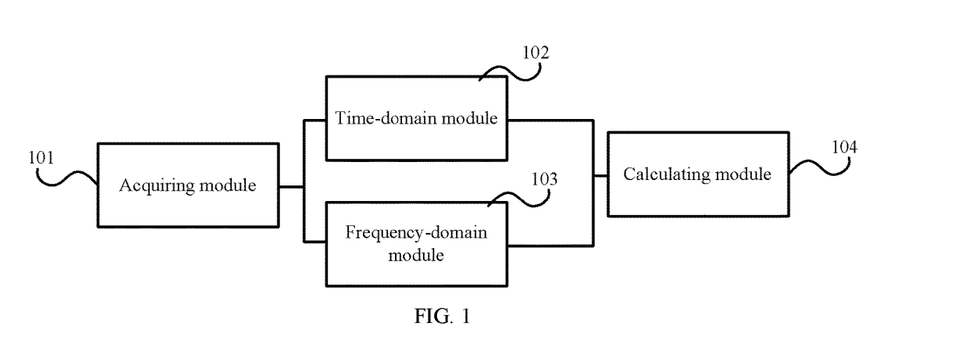
FIG. 1 is a schematic structural diagram of a heart rate detection apparatus according to a first embodiment of the present application.

FIG. 1 is a schematic structural diagram of a heart rate detection apparatus according to a first embodiment of the present application. As illustrated in FIG. 1, the heart rate detection apparatus according to this embodiment includes: an acquiring module 101, a time-domain module 102, a frequency-domain module 103 and a calculating module 104.

The acquiring module 101 is configured to acquire a plurality of time-domain heart rate detection data.

In this embodiment, the time-domain heart rate detection data specifically includes data effective in heart rate detection that is extracted by the acquiring module 101 from detection signals output by a heart rate sensor. Preferably, during acquiring the plurality of time-domain heart rate detection data, interference signals in the detection data may be filtered by using any one or combination of a finite impulse response (FIR) filter, an infinite impulse response (IIR) filter and an adaptive filter. Therefore, the acquiring module 101 in this embodiment may also be referred to as a signal processing module.

It should be noted that in this embodiment, the "acquiring a plurality of time-domain heart rate detection data" includes, but not limited to, acquiring the time-domain heart rate detection data by means of active extraction or passive reception or the like.

The time-domain module 102 is configured to: if the plurality of time-domain heart rate detection data includes a weak interference signal, extract a first feature point from the plurality of time-domain heart rate detection data, and collect statistics on feature data of the first feature point to determine time-domain heart rate detection data involved heart rate calculation.

In this embodiment, the first feature point includes peaks and valleys. Further, during collecting statistics on the feature data of the first feature point to determine the time-domain heart rate detection data used in calculating heart rate, the time-domain module 102 firstly collects statistics on amplitudes of a plurality of peaks and amplitudes of a plurality of valleys to determine a plurality of adjacent peak-valley amplitude differences, and then determines the time-domain heart rate detection data used in calculating heart rate according to the plurality of peak-valley amplitude differences.

The frequency-domain module 103 is configured to: if the plurality of time-domain heart rate detection data includes a strong interference signal, transform the plurality of time-domain heart rate detection data to a frequency domain to obtain a plurality of frequency-domain heart rate detection data, extract a second feature point from the plurality of frequency-domain heart rate detection data, and collect statistics on feature data of the second feature point to determine frequency-domain heart rate detection data used in calculating heart rate.

In this embodiment, the strength of the interference signal in the plurality of time-domain heart rate detection data may be specifically preliminarily judged according to a plurality of motion data of a motion sensor on the electronic terminal. For example, when a user wearing the electronic terminal is in a smooth motion state or is not moving, the plurality of motion data of the motion sensor has a small amplitude (for example, less than a set amplitude threshold), and in this case if the amplitude of the motion data is small, it indicates that the interference signal is weak, and on the contrary, the interference signal is strong.

The calculating module 104 is configured to calculate the heart rate according to the time-domain heart rate detection data or the frequency-domain heart rate detection data used in calculating heart rate.

The embodiment illustrated in FIG. 1 may further specifically applied to a specific electronic terminal, for example, a smart phone, a smart bracelet, a smart earphone or the like.

In the embodiments hereinafter of the present application, description is given by using the scenarios where the heart rate calculation is performed based on time-domain analysis when the interference signal in the plurality of time-domain heart rate detection data is weak and based on the frequency-domain analysis when the interference signal in the plurality of time-domain heart rate detection data is strong as examples.

In addition, it should be noted that in the following embodiments of the present application, the heart rate is calculated mainly based on the time-domain heart rate detection data corresponding to the peaks in the first feature point. However, in other embodiments, the heart rate may also be calculated based on the time-domain heart rate detection data corresponding to the valleys in the first feature point.

Figure 2:
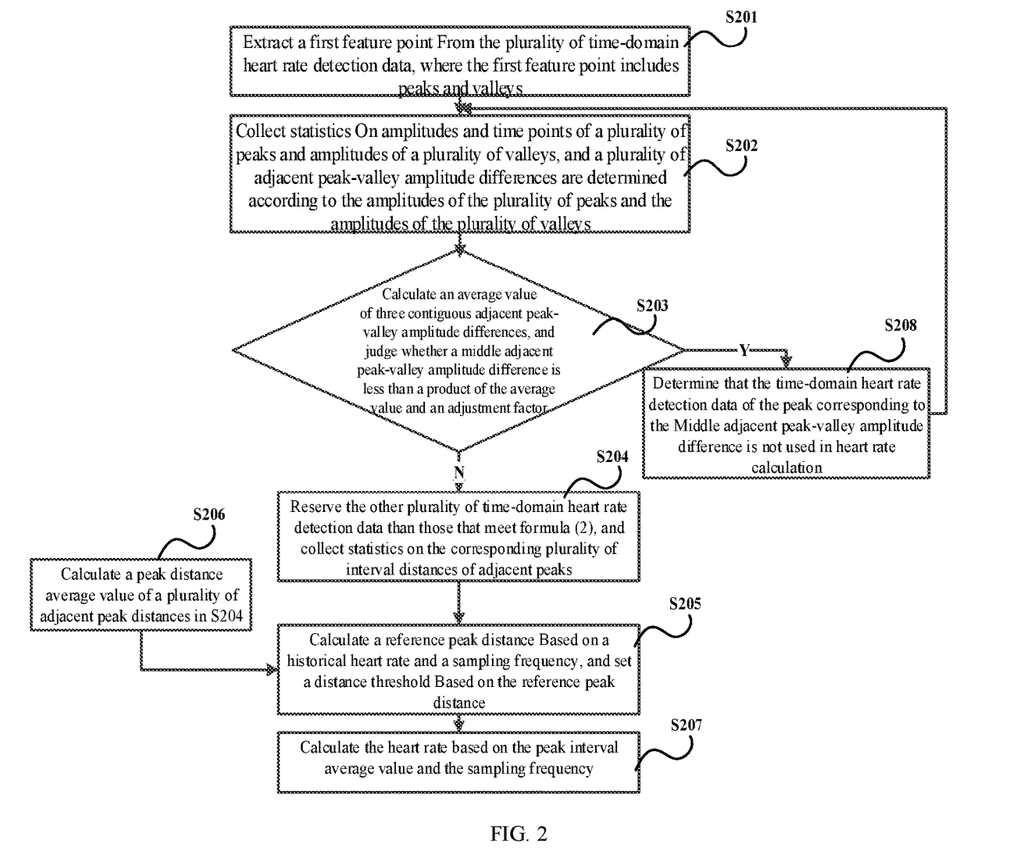
FIG. 2 is a schematic flowchart of a heart rate detection method according to a second embodiment of the present application.

FIG. 2 is a schematic flowchart of a heart rate detection method according to a second embodiment of the present application. In this embodiment, description is given by using the scenario where the heart rate calculation is performed based on the time-domain analysis when the interference signal in the plurality of time-domain heart rate detection data is weak as an example.

Specifically, in this embodiment, the heart rate detection method includes the following steps:

S201: A first feature point in the plurality of time-domain heart rate detection data is extracted, where the first feature point includes peaks and valleys.

S202: Statistics are collected on amplitudes and time points of a plurality of peaks and amplitudes of a plurality of valleys, and a plurality of adjacent peak-valley amplitude differences are determined according to the amplitudes of the plurality of peaks and the amplitudes of the plurality of valleys.

In this embodiment, statistics on the amplitudes and the time points of the plurality of peaks and the amplitudes of a plurality of valleys may be collected specifically by using a window function.

In this embodiment, the amplitude of the peak is represented by $peak_{amp}(n)$, and the time point of the peak is represented by $peak_{pos}(n)$, and the amplitude of the valley is represented by $valley_{amp}(n)$. Specifically, an adjacent peak-valley amplitude difference $amp(n)$ is represented by formula (1):

$$amp(n)=peak_{amp}(n)-valley_{amp}(n) \qquad (1)$$

In formula (1), n=1, ..., N−1, where N represents the number of peaks and the number of valleys respectively. In formula (1), $amp(n)$ represents the $n^{th}$ amplitude between specific adjacent peaks and valleys, $peak_{amp}(n)$ represents the amplitude of the $n^{th}$ peak, and $valley_{amp}(n)$ represents the amplitude of the $n^{th}$ valley. For example, $amp(1)$ represents an amplitude difference between the first peak and the first valley, $amp(2)$ represents an amplitude difference between the second peak and the second valley, and so on.

Assume that there are 12 first feature points including 6 peaks and 6 valleys, then in formula (1), N=6, n=0, 1, 2, 3, 4, 5, and $amp(n)$ is a difference between the amplitude of the $n^{th}$ peak and the amplitude of the $n^{th}$ valley, that is, an amplitude difference.

During the heart rate calculation, if the calculation is based on the following assumption: with respect to adjacent peaks and valleys, the peaks occur prior to the valleys, during determining the amplitude difference, the amplitude of time-domain heart rate detection data corresponding to a close following valley is subtracted from the amplitude of time-domain heart rate detection data of a previous peak of the valley. However, it should be noted that determining the heart rate is not absolutely based on the above assumption, but may be based on other assumptions. In this case, during determining the above amplitude difference, the sequence or positions of two pieces of time-domain heart rate detection data used in difference calculation may be flexibly defined.

S203: An average value of three contiguous adjacent peak-valley amplitude differences is calculated, and whether a central adjacent peak-valley amplitude difference is less than a product of the average value and an adjustment factor is judged; and if the middle adjacent peak-valley amplitude difference is less than the product of the average value and the adjustment factor, if not, step S204 is performed, and otherwise, step S208 is performed.

In this embodiment, if the average value of the three contiguous adjacent peak-valley amplitude differences is calculated, whether the central peak-valley amplitude differences is less than the product of the average value and the adjustment factor is judged according to formula (2):

$$amp(n)<\lambda 1*[amp(n-1)+amp(n)+amp(n+1)]/3 \qquad (2)$$

In formula (2), $amp(n)$ represents the nth amplitude difference between adjacent peaks and valleys, $amp(n-1)$ represents the $n-1^{th}$ amplitude difference between adjacent peaks and valleys, $amp(n+1)$ represents the $n+1^{th}$ amplitude difference between adjacent peaks and valleys, and $\lambda 1$ represents the adjustment factor, where the accuracy of the calculated heart rate may be controlled by controlling the value of $\lambda 1$.

Referring to formula (2), an average sum of the $n^{th}$ amplitude difference, the $n-1^{th}$ amplitude difference and the $n+1^{th}$ amplitude difference is the amplitude difference average value. If the nth amplitude difference is less than a product of the amplitude difference average value and the adjustment factor $\lambda$, it indicates that the time-domain heart rate detection data of the peak corresponding to the nth amplitude difference is not used in the subsequent heart rate calculation, and the time-domain heart rate detection data corresponding to the $n-1^{th}$ amplitude difference and the $n+1^{th}$ amplitude difference is reserved for further judgment in step S206 on whether the time-domain heart rate detection data is the final time-domain heart rate detection data used in calculating heart rate.

It should be noted that in this embodiment, description is given by only using the scenario where three contiguous adjacent peak-valley amplitude differences are statistically collected as an example, and an average value of other plural adjacent peak-valley amplitude differences may also be calculated, for example, an average value of an odd number of adjacent peak-valley amplitude differences.

S204: The other plurality of time-domain heart rate detection data than those that meet formula (2) is reserved, and the corresponding plurality of adjacent peak distances is statistically collected.

In this embodiment, the adjacent peak distances $dis_{peak}(n)$ are statistically collected by using formula (3):

$$dis_{peak}(n)=peak_{pos}(n+1)-peak_{pos}(n) \qquad (3)$$

In formula (3), $dis_{peak}(n)$ represents a distance between adjacent peaks, for example, a distance between the $n+1^{th}$ peak and the $n^{th}$ peak, where the distance is used as a time statistical value, and for example, a first distance $dis_{peak}(1)$ between adjacent peaks is a distance between the second peak and the first peak, a second distance $dis_{peak}(2)$ between adjacent peaks is a distance between the third peak and the second peak, and so one.

Assume that there are 12 first feature points including 6 peaks and 6 valleys, then in the above formula, N=6, n=0, 1, 2, 3, 4, 5, and $dis_{peak}(n)$ is a distance between the $n+1^{th}$ peak and the $n^{th}$ peak.

However, in this embodiment, the specific numbers of the first feature points, the peaks and the valleys are defined herein only for clear description of the technical solutions of the present application instead of construing any limitation.

S205: A reference peak distance is calculated according to a historical heart rate and a sampling frequency, and a distance threshold is set according to the reference peak distance.

In this embodiment, considering that miss-acquisition may occur during the process of acquiring the time-domain heart rate detection data, a first distance threshold and a second distance threshold are meanwhile set while the distance threshold is set, to determine whether miss-acquisition occurs.

Specifically, the specific method for defining the first distance threshold or the second distance threshold according to the historical heart rate is as follows:

First, the reference peak distance (or referred to as a peak reference distance) is calculated according to the historical heart rate and the sampling frequency of the time-domain heart rate detection data.

As specifically illustrated in formula (4), fs represents the sampling frequency, $HB_{ref}$ represents the historical heart rate in the unit of beats/second, where the historical heart rate may be an effective heart rate that is most proximate to the current time point or an average value of a plurality of effective heart rates that are proximate to the current time point, and $dis_{ref}$ represents the reference peak distance.

$$dis_{ref} = \frac{60 * fs}{HB_{ref}} \qquad (4)$$

Further, the first distance threshold and the second distance threshold are set according to the reference peak distance. The first distance threshold includes a first distance upper threshold and a first distance lower threshold, and the second distance threshold includes a second distance upper threshold and a second distance lower threshold.

In this embodiment, the first distance upper threshold and the first distance lower threshold respectively represent a maximum distance and a minimum distance between adjacent peaks in case of no data packet loss, and the second distance upper threshold and the second distance upper limit respectively represent a maximum distance and a minimum distance between adjacent peaks in case of data packet loss. That is, a peak (or referred to as an un-acquired peak is present) is defaulted. The first distance upper threshold, the first distance lower threshold, the detailed definition rules of the second distance upper threshold and the second distance lower threshold are as listed in formula (5).

$$dis_{thup\ 1} = \delta_1 * dis_{ref}$$

$$dis_{thdown\ 1} = \delta_2 * dis_{ref}$$

$$dis_{thup\ 2} = \delta_3 * dis_{ref}$$

$$dis_{thdown\ 2} = \delta_4 * dis_{ref} \qquad (5)$$

In formula (5): $Dis_{thup1}$ represents the first distance upper threshold, $dis_{thdown1}$ represents the first distance lower threshold, $dis_{thup2}$ represents the second distance upper threshold, $dis_{thdown2}$ represents the second distance lower threshold, $\delta_1, \delta_2, \delta_3$ and $\delta_4$ represent the adjustment factors, where $\delta_1$ is generally a number greater than 1, $\delta_2$ is generally a number less than or equal to 1, and $\delta_1$ and $\delta_2$ essentially represent upper and lower threshold parameters of a peak distance, $\delta_3$ is generally a number greater than or equal to 2, $\delta_4$ is generally a number less than or equal to 2 and greater than 1, and $\delta_3$ and $\delta_4$ are upper and lower threshold parameters of the distance between two peaks that are set for compensation for the lost peaks.

In formula (5), $\delta_1, \delta_2, \delta_3$ and $\delta_4$ are related to the motion state of the user, personal physiological conditions of the user (for example, age, gender, weight, heart characteristics and the like factors), and may be automatically provided by the user and constantly iteratively updated by recording and learning by the system. For example, at the beginning of the motion, the heart rate increases at a high speed, and thus $[\delta_2, \delta_1]$ and $[\delta_4, \delta_3]$ need to be set at a larger interval; however, after the motion for a period of time, the heart rate is in a high state. When the motion strength does not change greatly, the heart rate of the human body should be kept at a high and stable value, and in this case, the $[\delta_2, \delta_1]$ and $[\delta_4, \delta_3]$ need to be defined to a smaller interval. Still for example, the heart rate of the old changes slowly, and thus $[\delta_2, \delta_1]$ and $[\delta_4, \delta_3]$ need to be defined to a smaller interval or the like, and so on.

It should be noted that $\delta_3$ and $\delta_4$ are directed to the scenario where the time-domain heart rate detection data corresponding to a peak is not acquired. However, it should be further noted that if with respect to the scenario where the time-domain heart rate detection data corresponding to at least two peaks is not acquired, the issue may be addressed by adjusting the values of $\delta_3$ and $\delta_4$.

The specific method for determining the time-domain detection signal used in calculating heart rate according to the distance between adjacent peaks, and the defined first distance threshold and second distance threshold is as follows:

$$dis_{thdown\ 1} \leq dis_{peak}(n) \leq dis_{thup\ 1} \qquad (6)$$

$$dis_{thdown\ 2} \leq dis_{peak}(n) \leq dis_{thup\ 2} \qquad (7)$$

Judgment is firstly performed by using formula (6). If $dis_{peak}(n)$ does not satisfy formula (6), and it is further judged that $dis_{peak}(n)$ does not satisfy formula (7) either, the time-domain detection signal of the peak corresponding to $dis_{peak}(n)$ is not used in calculating heart rate.

It should be noted that in this embodiment, as described above, the scenario where during acquiring the time-domain heart rate detection data, miss-acquisition of the time-domain heart rate detection data corresponding to the peaks may occur is mainly considered, that is, the number peaks is less than the current number of peaks, and as a result, the heart rate detection is incorrect. Therefore, the first distance threshold and the second distance threshold are defined. If $dis_{peak}(n-1)$ satisfies formula (6), for example, $dis_{peak}(n)$ does not satisfy formula (6) and does not satisfy formula (7) either, it indicates that miss-acquisition of the time-domain heart rate detection data occur, and the time-domain heart rate detection of the $n+1^{th}$ peak corresponding to $dis_{peak}(n)$ not satisfying formula (7) is not used in the final heart rate calculation.

In addition, it should be noted that in another application scenario, the scenario where the time-domain heart rate detection data may be excessively acquired. Specifically, if $dis_{peak}(n) < dis_{thdown1}$, and $dis_{peak}(n-1)$ satisfies formula (6), the time-domain heart rate detection data corresponding to the $n+1^{th}$ peak forming $dis_{peak}(n)$ is not used in the final heart rate calculation.

In addition, it should be noted that in other embodiments, if it is ensured that miss-acquisition of the above time-domain heart rate detection data do not occur, formula (7) may also be not included or not executed.

S206: A peak distance average value of a plurality of adjacent peak distances in S204 is calculated.

In this embodiment, a distance sum of a plurality of reserved adjacent distances is firstly calculated, and then the calculated distance sum is divided by the total number of distances between adjacent peaks, such that the peak distance average value is obtained.

Figure 3:
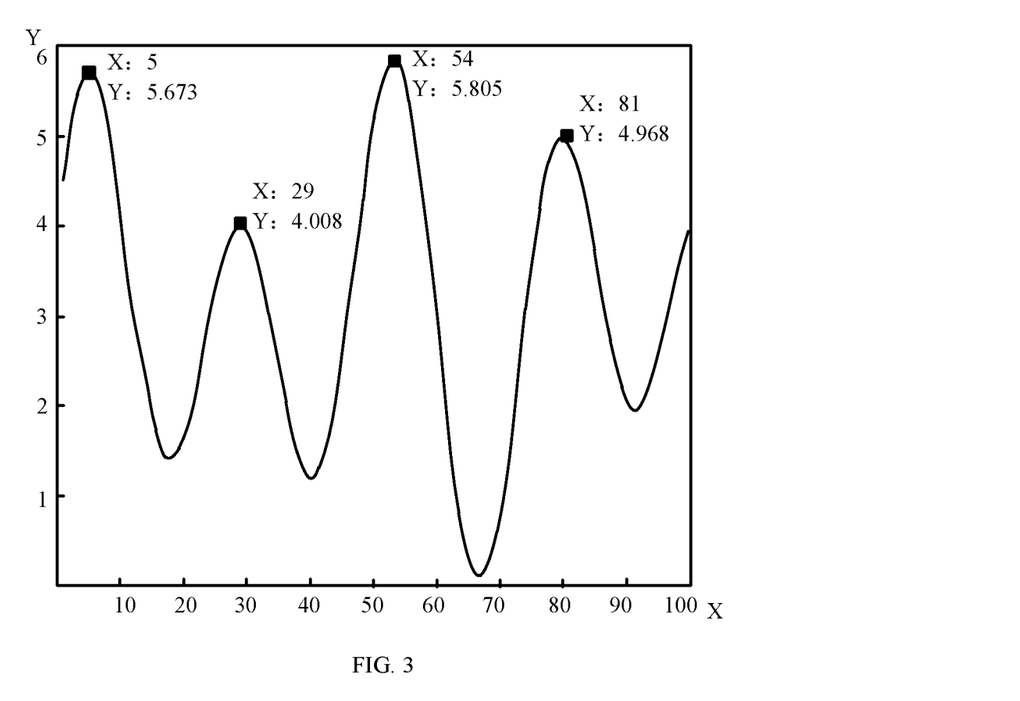
FIG. 3 is an exemplary schematic diagram of a waveform of time-domain heart rate detection data according to a third embodiment of the present application.

FIG. 3 is an exemplary schematic diagram of a waveform of time-domain heart rate detection data according to a third embodiment of the present application. As illustrated in FIG. 3, assume that there are 4 peaks, and miss-acquisition of the peaks does not occur, then the total number of peak distances is 3 in practice, and the total distance of the calculated peak distance by using formula (8) is sum=76, and the peak distance average value is 76/3=25.3.

It should be noted that in the scenario where miss-acquisition of the peaks does not occur as illustrated in FIG. 3, the total distance sum of the peak distances may be calculated according to formula (8):

$$m_1 = m_1 + 1, \text{Sum} = \text{Sum} + \text{dis}_{peak}(m_1) \qquad (8)$$

Figure 4:
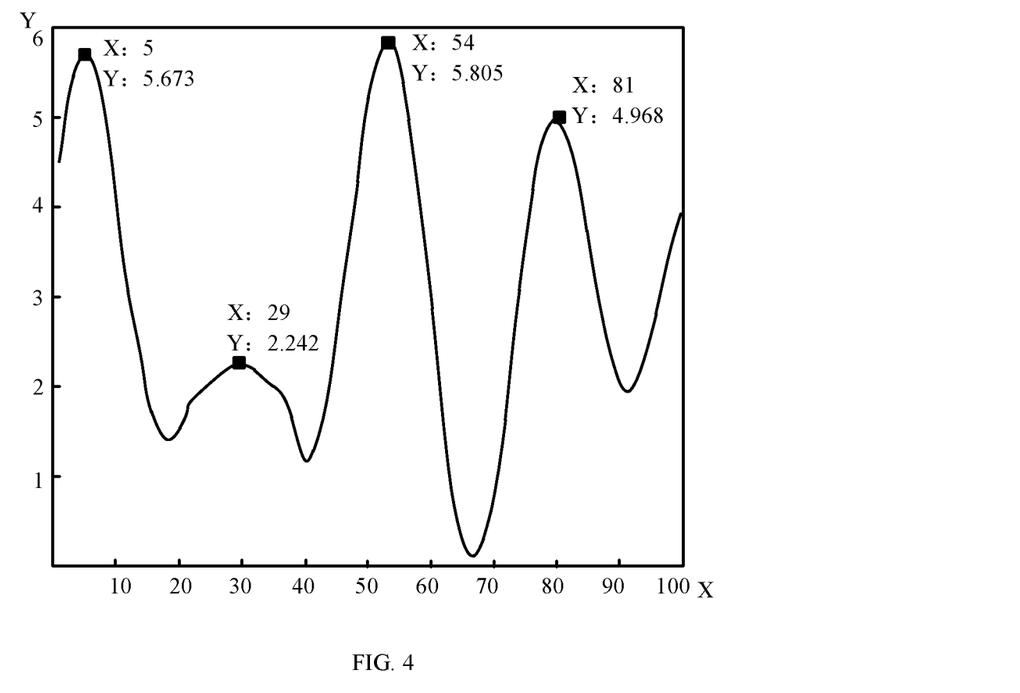
FIG. 4 is an exemplary schematic diagram of a waveform of time-domain heart rate detection data according to a fourth embodiment of the present application.

FIG. 4 is an exemplary schematic diagram of a waveform of time-domain heart rate detection data according to a fourth embodiment of the present application. As illustrated in FIG. 4, assume that there are 4 peaks in practice but there is one peak (29, 2.2242) is not detected, then when it is determined according to formula (6) and formula (7) that a peak (for example, (29, 2.2242) not detected is present between two contiguous peaks, the total distance sum of the peak distances is calculated according to formula (9):

$$m_1 = m_1 + 2, \text{Sum} = \text{Sum} + \text{dis}_{peak}(m_1) \qquad (9)$$

In formula (9), during iteration, the number of peaks of the first feature point is compensated by ensuring that $m_1=m_1+2$. In formula (8) and formula (9), $\text{dis}_{peak}(m_1)$ represents the $m_1^{th}$ peak distance.

In this embodiment, after the total distance sum of the peak distances is calculated according to formula (8) and formula (9), the peak distance average value $\text{Avg}_{dis}$ is calculated according to formula (10).

$$Avg_{dis} = \frac{\text{sum}}{M} \qquad (10)$$

In formula (10), M represents the total number of peak distances.

It should be noted that if miss-detection of the peak is not present between adjacent peaks, the distance is calculated according to formula (8); and if miss-detection of the peak is present between the subsequent adjacent peaks, formula (9) is executed based on the total distance sum calculated according to formula (8).

In addition, in some embodiments, if it is determined that no peak misses detection, the total distance of the peak distances is calculated only according to formula (8), or operation of formula (9) is not executed to calculate the total distance sum of the peak distances.

S207: The heart rate is calculated according to the peak interval average value and the sampling frequency.

In this embodiment, the heart rate may be specifically determined according to formula (11):

$$HB_{curtemp} = \frac{fs * 60}{Avg_{dis}} \qquad (11)$$

In formula (11), $HB_{curtemp}$ represents the heart rate, fs represents the sampling frequency of the time-domain heart rate detection data, and $Avg_{dis}$ represents the above peak distance average value.

S208: The time-domain heart rate detection data of the peak corresponding to the central adjacent peak-valley amplitude difference is not used in calculating heart rate.

In this embodiment, the time-domain heart rate detection data obtained in step S208 may be considered as the time-domain heart rate detection data that is subject to the interference and thus is not used in calculating heart rate.

It should be noted that in the above embodiment, as seen from the waveforms formed by the plurality of time-domain heart rate detection data, the corresponding positions of the peaks and valleys are used as the first feature point, and correspondingly, the peak corresponds to one piece of time-domain heart rate detection data, and the valley corresponds to another piece of time-domain heart rate detection data. However, in other embodiments, the first feature point may also be the position proximate to the peak and the valley on the waveform of the time-domain heart rate detection data, e.g., the position where a tangent slope is maximum on two sides of the peak and the valley.

It should be noted that in the above embodiment, the time-domain heart rate detection data corresponding to the peak is used in the final heart rate calculation. Nevertheless, in other embodiments, the time-domain heart rate detection data corresponding to the valley may also be used in the final heart rate calculation, and the peak achieves the same effect as the valley in the above embodiment.

Figure 5:
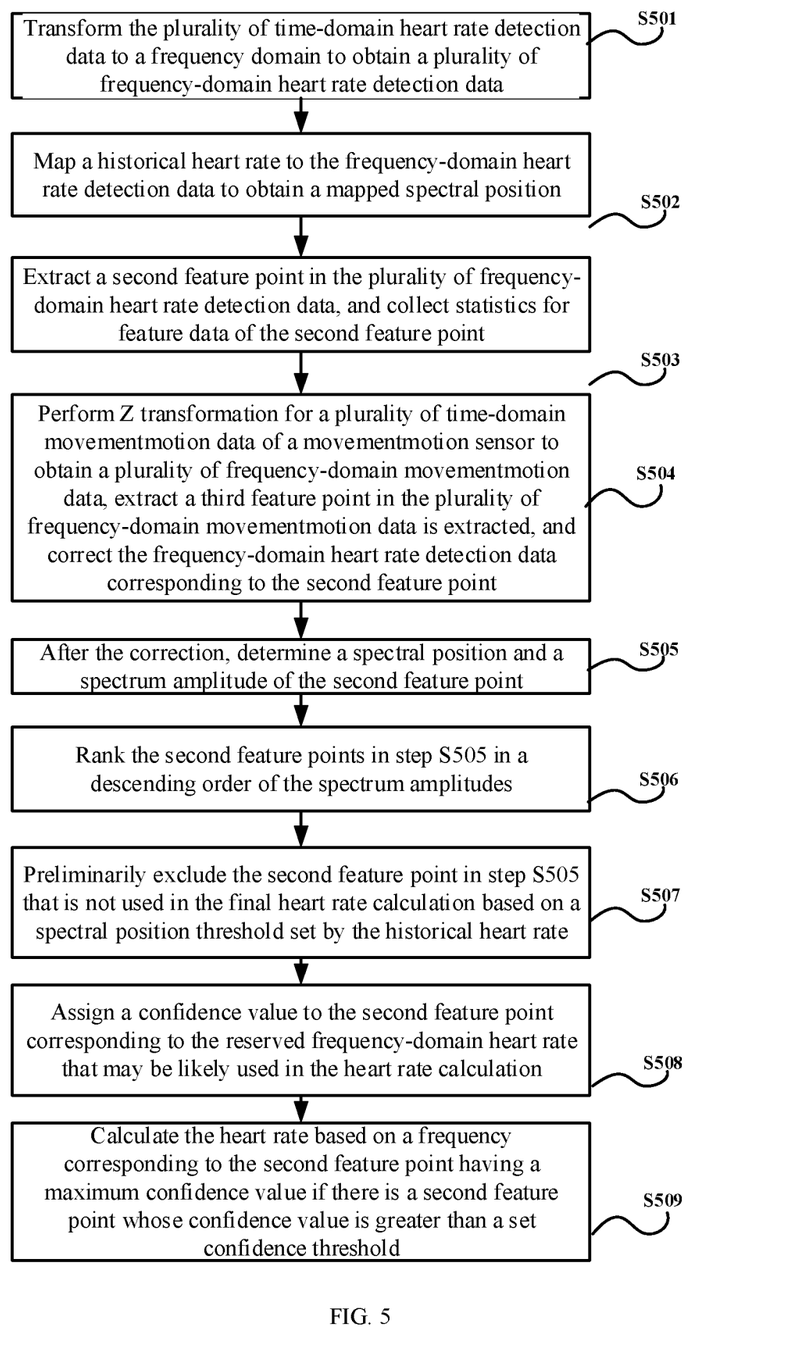
FIG. 5 is a schematic flowchart of a heart rate detection method according to a fifth embodiment of the present application.

FIG. 5 is a schematic flowchart of a heart rate detection method according to a fifth embodiment of the present application. As illustrated in FIG. 5, in this embodiment, description is given by using the scenario where the heart rate is detected based on the frequency-domain analysis when the interference signal is strong as an example.

Specifically, in this embodiment, the heart rate detection method includes the following steps:

S501: The plurality of time-domain heart rate detection data is transformed to a frequency domain to obtain a plurality of frequency-domain heart rate detection data.

In this embodiment, the time-domain heart rate detection data obtained in the above first embodiment is subjected to curve Z transformation, such that the frequency-domain heart rate detection data is obtained. The specific transformation is as listed in formula (12) to formula (14).

$$\theta_0 = \frac{2\pi * f_1}{f_s} \qquad (12)$$
$$A = e^{j\theta_0}$$

In formula (12), $f_1$ represents a frequency lower threshold of the frequency-domain analysis, $f_s$ represents a sampling frequency, $\theta_0$ represents an initial phase of the frequency-domain analysis, and A represents an initial phase parameter.

$$\varphi_0 = \frac{2\pi * \Delta f}{f_s} \qquad (13)$$
$$W = e^{j\varphi_0}$$

In formula (13), $\Delta f$ represents a resolution of spectrum analysis, $\varphi_0$ represents a precision of frequency-domain analysis, and W represents a precision parameter.

$$M = \frac{f_2 - f_1}{\Delta f} \qquad (14)$$
$$z_k = A W^{-k}$$

In formula (14), $f_2$ represents a frequency upper threshold of the frequency-domain analysis, k=0, . . . , M−1, M represents the number of spectral lines of the frequency-domain analysis, one spectrum line corresponds to one spectral line position, and $z_k$ represents a transformation expression of the curve Z transformation.

The frequency-domain heart rate detection data finally obtained according to formula (11) to formula (14) is as represented by formula (15):

$$\text{freq}_{ppg}(z_k) = \Sigma_{i=0}^{I-1} \text{ppg}(i) z_k^{-i} = \Sigma_{i=0}^{I-1} \text{ppg}(i) A^{-i} W^{ik} \quad (15)$$

In formula (15), I represents the number of buffered time-domain heart rate detection data, and ppg(i) represents the $i^{th}$ time-domain heart rate detection data.

S502: A historical heart rate is mapped to the frequency-domain heart rate detection data to obtain a mapped spectral position.

In this embodiment, the mapped spectral position of the historical heart rate on the frequency-domain heart rate detection data is specifically obtained according to formula (16).

$$\text{freq}_{preHB} = \frac{HB_{pre} - 60 * f_1}{\Delta f} \quad (16)$$

In formula (16), $HB_{pre}$ represents the historical heart rate, $\text{freq}_{preHB}$ represents the mapped spectral position of the historical heart rate on the frequency-domain heart rate detection data, and $\Delta f$ and $f_1$ may be referenced to the above parameter description of the curve Z transformation of the time-domain heart rate detection data.

S503: A second feature point in the plurality of frequency-domain heart rate detection data is extracted, and feature data of the second feature point is statistically collected.

In this embodiment, the second feature point includes a relative maximum value point in the plurality of frequency-domain heart rate detection data. According to formula (15), a frequency-domain amplitude and a spectral position of the second feature point in the frequency-domain heart rate detection data are further statistically collected. Specifically, the a statistical value of the frequency-domain amplitude of the second feature point is specifically an amplitude corresponding to the relative maximum value point, and the statistical value of the spectral position of the second feature point is specifically a spectral line position corresponding to the relative maximum value point.

In the above disclosure, the frequency lower threshold $f_1$ of the frequency-domain analysis and the frequency upper threshold $f_2$ of the frequency-domain analysis may be defined by reference to a frequency range of the actual heart rate. For example, generally the heart rate has a frequency of 0.5 to 4 Hz, and in this case, the frequency lower threshold $f_1$ of the frequency-domain analysis may be 0.5 Hz, and the frequency upper threshold $f_2$ of the frequency-domain analysis may be 4 Hz. If the harmonic is considered, the frequency of the heart rate is 1 to 8 Hz, and in this case, the frequency lower threshold $f_1$ of the frequency-domain analysis may be 1 Hz, and the frequency upper threshold $f_2$ of the frequency-domain analysis may be 8 Hz.

In this embodiment, the frequency upper and lower thresholds of the frequency-domain analysis may be defined, such that the total workload of the data processing is reduced, and the efficiency of data processing is effectively improved.

S504: Z transformation is performed for a plurality of time-domain motion data of a motion sensor to obtain a plurality of frequency-domain motion data, a third feature point in the plurality of frequency-domain motion data is extracted, and the frequency-domain heart rate detection data corresponding to the second feature point is corrected.

Similar to the frequency-domain heart rate detection data, the Z transformation is performed for the time-domain motion data of the motion sensor, such that the finally obtained and output frequency-domain motion data is as illustrated by formula (17):

$$\text{freq}_{acc}(z_k) = \Sigma_{j=0}^{J-1} \text{acc}(j) z_k^{-j} = \Sigma_{i=0}^{J-1} \text{acc}(j) A^{-j} W^{jk} \quad (17)$$

In formula (17), J represents the number of buffered time-domain motion data, acc(j) represents the $j^{th}$ time-domain motion data, k=0, . . . , M−1, M represents the number of spectral lines of the frequency-domain analysis, and one spectral line corresponds to one spectral line position.

Figure 6:
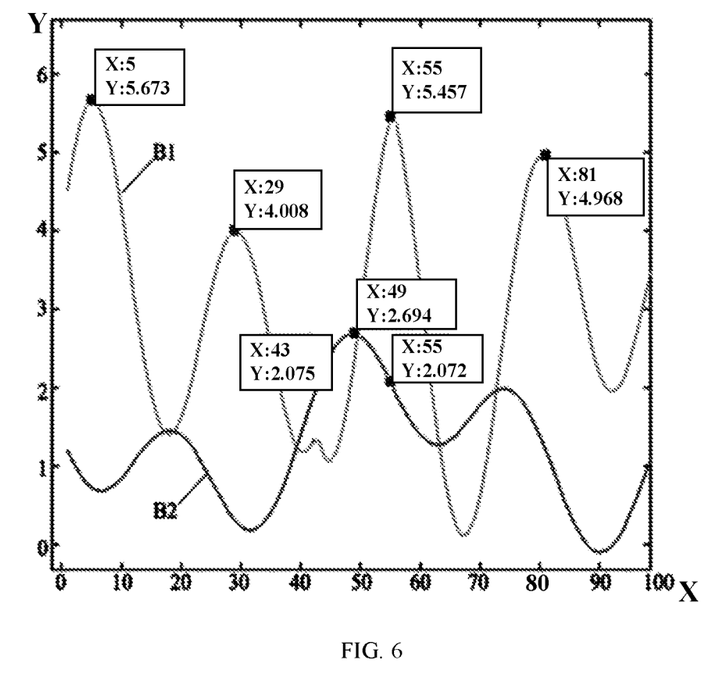
FIG. 6 is an exemplary schematic diagram of frequency-domain heart rate detection data and frequency-domain motion data according to a sixth embodiment of the present application.

Referring to FIG. 6, a schematic diagram of frequency-domain heart rate detection data and frequency-domain motion data according to a sixth embodiment of the present application is given. In FIG. 6, B1 represents a waveform formed by the frequency-domain heart rate detection data, and B2 represents a waveform formed by the frequency-domain motion data. In FIG. 6, coordinate X represents a spectral position, and coordinate Y represents a spectrum amplitude. For example, in a specific example, with respect to the frequency-domain heart rate detection data, a minimum value of the spectral position x is 1 and a maximum value of the spectral position x is 100, and a minimum value of the spectrum amplitude y is 0.2 and a maximum value of the spectrum amplitude y is 5.673.

As described above, similar to the second feature point, the third feature point is also a relative maximum value point on the frequency-domain motion data. Each relative maximum value point corresponds to different amplitudes and spectral positions. That is, a statistical value of the frequency-domain amplitude of the third feature point is the amplitude of the relative maximum value point, and a statistical value of the spectral prostitution is a spectral line position of the relative maximum value point.

In this embodiment, it should be noted that, the number of buffered time-domain motion data may be the same as, or different from the number of buffered time-domain heart rate detection data. The acquisition frequency of the time-domain motion data may be the same as, or different from, the acquisition frequency of the time-domain heart rate detection data. The frequency lower threshold of the spectrum analysis and the frequency upper threshold of the spectrum analysis of the frequency-domain motion data may be respectively the same as, or different from the frequency lower threshold of the spectrum analysis and the frequency upper threshold of the spectrum analysis of the frequency-domain heart rate detection data; and the precision of the spectrum analysis of the frequency-domain motion data may be the same as, or different from the precision of the spectrum analysis of the frequency-domain heart rate detection data. The parameters for the above spectrum analysis may be specifically defined according to the application scenario.

In this embodiment, when the frequency-domain heart rate detection data corresponding to the second feature point is corrected according to the third feature point, the frequency-domain heart rate detection data to be used in the correction may be determined according to the third feature point, the first frequency-domain threshold and the second frequency-domain threshold, and then the frequency-domain heart rate detection data used in the correction and the frequency-domain heart rate detection data corresponding to the second feature point are corrected according to a fitting model of interference fitting.

In a specific application scenario, the process of correcting the frequency-domain heart rate detection data corresponding to the second feature point is as follows:

Firstly, the frequency-domain motion data of the motion sensor is analyzed to determine a plurality of third feature points having a relative maximum value, that is, the relative maximum value points, where different maximum value points are located at different spectral line positions; and then a maximum value point is determine, where the maximum value point reflects the position of a strongest interference signal. The amplitude of the maximum value point is affected by the strongest interference signal. However, generally, the interference signal also has a bandwidth range.

Accordingly, to thoroughly exclude the frequency-domain heart rate detection that is not used in calculating heart rate, a corresponding frequency-domain amplitude threshold is defined according to the amplitude of the maximum value point. It is considered that the frequency-domain motion data is affected by the interference signal as long as the frequency-domain amplitude threshold is exceeded.

The bandwidth of the interference signal may be determined according to the spectral position of the frequency-domain motion data that is affected by the interference signal. That is, it may be considered that the second feature point in a spectral position range defined by the defined frequency-domain amplitude threshold at the spectral position on the frequency-domain heart rate detection data is most likely affected by the interference signal, and thus the second feature point in the spectral position range defined by the frequency-domain amplitude threshold needs to be corrected.

For example, still using the scenario where the third feature point is the relative maximum value point as an example, assume that the frequency-domain motion data of the motion sensor is reflected on the corresponding 8 spectral lines, the maximum value is present on the seventh spectral line, the amplitude thereof is A, the maximum value is on the left side, the spectral position where the amplitude exceeds A-d most likely includes the interference signal (the spectral line position where the amplitude exceeds A-d corresponds to the reserved first third feature point), on the right side, the spectral line position where the amplitude exceeds A-D most likely includes the interference signal (the spectral line position where the amplitude exceeds A-D corresponds to the reserved last third feature point). Therefore, by means of defining the frequency-domain amplitude thresholds A-d and A-D, the bandwidth of the interference is determined, the bandwidth of the interference signal is the range defined by the spectral line positions corresponding to the two amplitude thresholds, and the second feature point in the same spectral position range needs to be corrected. Accordingly, the defined frequency-domain amplitude threshold includes an upper threshold and a lower threshold.

In a specific application scenario, the second feature point is specifically corrected by means of the following fitting interference processing, as illustrated in formula (18):

$$\text{freq}'_{ppg}(n') = \text{freq}_{ppg}(n') - \lambda * \text{win}_{func}(n') * \text{freq}_{acc}(n'),$$
$$n' = n_1 \ldots n_2 \quad (18)$$

In formula (18), $\text{freq}'_{ppg}(n')$ represents the frequency-domain heart rate detection data corresponding to the corrected second feature point; $\text{win}_{func}(n')$ represents a correction window function, where the window function is used as a fitting model for interference fitting of the reserved third feature point and may be a cosine, Gaussian or another type of window function; $\text{freq}_{acc}(n')$, represents the reserved third feature point that most likely include the interference signal, the number of third feature points is $n_2 - n_1$; $\text{freq}_{ppg}(n_1)$ represents the first second feature point that has the same spectral position as the first reserved third feature point $\text{freq}_{acc}(n_2)$; and $\text{freq}_{ppg}(n_2)$ represents the last second feature point that has the same spectral position as the last reserved third feature point $\text{freq}_{acc}(n_2)$.

Figure 7:
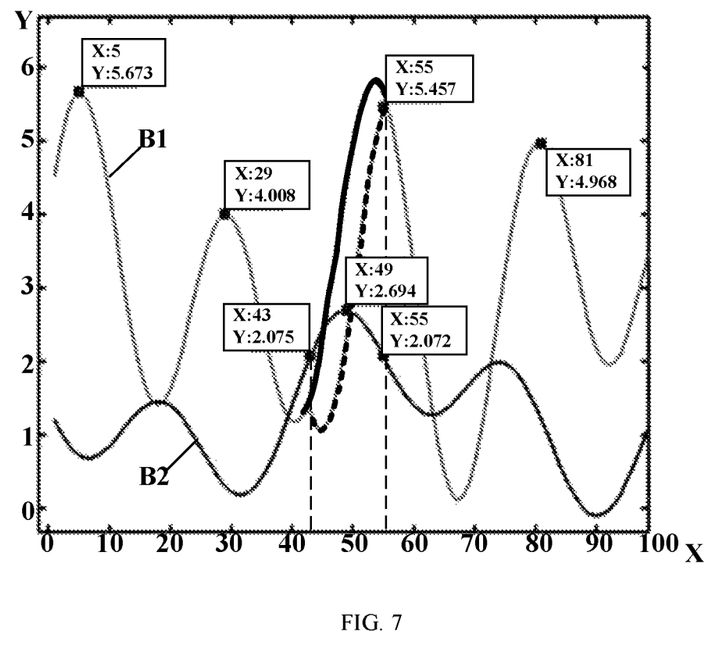
FIG. 7 is a schematic diagram of a determined interference signal bandwidth range and a corrected second feature point according to a seventh embodiment of the present application.

FIG. 7 is a schematic diagram of a determined interference signal bandwidth range and a corrected second feature point according to a seventh embodiment of the present application. As illustrated in FIG. 7, the horizontal coordinate represents the spectral position, and the vertical coordinate represents the spectrum amplitude, the maximum value point in all the relative maximum value points on the frequency-domain motion data is located at (44, 2.694), the upper threshold and the lower threshold of the frequency-domain amplitude threshold that are defined according to the maximum value point are respectively 2.075 and 2.072. The frequency-domain motion data is greater than either of the two frequency-domain amplitude thresholds may be considered as being affected by the interference signal. On the second feature point, these two frequency-domain amplitude thresholds respectively correspond to spectral positions 43 and 45. Therefore, the bandwidth of the interference signal may be considered to be [43, 45], and the second feature point whose spectral position falls within the bandwidth range needs to be corrected.

In FIG. 7, on a waveform B2 of the frequency-domain motion data, [(43, 2.075), (55, 2.072)] is a region that is greatly affected by the interference signal; on a waveform B1 of the frequency-domain heart rate detection data, the dotted-line block represents the frequency-domain heart rate detection data that is greatly affected by the interference signal, and the frequency-domain heart rate detection data corresponding to the corrected second feature point is represented by the solid-line block. As seen from FIG. 7, before and after the correction, a statistical value of the second spectrum amplitude and a statistical value of the second spectral position of the second feature point have changed.

S505: After the correction, a spectral position and a spectrum amplitude of the second feature point are determined.

As illustrated in FIG. 7, after the correction, the second feature point include four relative maximum value points (5, 5.673), (29, 4.008), (55, 5.457) and (81, 4.968), where the uncorrected second feature point and the corrected second feature point are included.

S506: The second feature points in step S505 are ranked in a descending order of the spectrum amplitudes.

Specifically, as illustrated in FIG. 7, the ranked second feature points are: (5, 5.673), (55, 5.457), (81, 4.968) and (29, 4.008).

S507: The second feature point in step S505 that is not used in the final heart rate calculation is preliminarily excluded according to a spectral position threshold defined by the historical heart rate.

In this embodiment, the second feature point in step S505 that is not used in the final heart rate calculation is specifically preliminarily excluded according to formula (19):

$$\text{freq}_{preHB} - \delta_{freq} \leq \text{peak}'_{ppg}(x) \leq \text{freq}_{preHB} + \delta_{freq} \quad (19)$$

In formula (19), $\delta_{freq}$ represents a spectral position bandwidth adjustment factor, $\text{freq}_{preHB} - \delta_{freq}$ and $\text{freq}_{preHB} + \delta_{freq}$ respectively represent a lower threshold and an upper threshold in the spectral position threshold, and $\text{peak}'_{ppg}(x)$ represents the spectral position of the corrected second feature point.

Further, the frequency-domain heart rate detection data corresponding to the second feature point satisfying formula (19) is reserved. The reserved frequency-domain heart rate detection data corresponding to the second feature point may be likely the data used in calculating heart rate, and the unreserved frequency-domain heart rate detection data may be frequency-domain heart rate detection data that is not used in calculating heart rate.

S508: A confidence value is assigned to the second feature point corresponding to the reserved frequency-domain heart rate that may be likely used in calculating heart rate.

In this embodiment, the confidence value may be calculated based on one or a plurality of the following combinations:

a distance between a spectrum position of the second feature point of the frequency-domain heart rate detection data used in calculating heart rate, and a spectrum position of the historical heart rate in the frequency-domain heart rate detection data;

a distance between the spectrum position of the second feature point of the frequency-domain heart rate detection data used in calculating heart rate, and a spectrum position of the third feature point;

a bandwidth feature of the second feature point of the frequency-domain heart rate detection data used in calculating heart rate; and an amplitude of the second feature point of the frequency-domain heart rate detection data used in calculating heart rate.

Specifically, in this embodiment, the assigning a confidence value to the second feature point according to the spectral position of the second feature point and the mapped spectral position of the historical heart rate on the frequency-domain heart rate detection data may specifically include: assigning the confidence value to the second feature point based on the spectral position of the second feature point and the mapped spectral position of the historical heart rate on the frequency-domain heart rate detection data, and assigning the confidence value to the second feature point based on the spectral position of the second feature point and a Q-fold mapped spectral position of the historical heart rate on the frequency-domain heart rate detection data.

The above confidence value assignment is described by using the scenario where the second feature point and the third feature point are both the relative maximum value points as an example.

After the correction, a distance E1 between the spectral position $peak'_{ppg1pos}$ of the second feature point and the mapped spectral position $freq_{preHB}$ of the historical heart rate on the frequency-domain heart rate detection data is determined.

After the correction, a distance E2 between the spectral position $peak'_{ppg1pos}$ of the second feature point and the Q-fold mapped spectral position $freq_{preHB}$ of the historical heart rate on the frequency-domain heart rate detection data is determined. The Q-fold is mainly based on consideration of the existence of the harmonic in the frequency-domain heart rate detection data. If a primary harmonic is existent, Q takes a value of 1; if a secondary harmonic is existent, Q takes a value of 2; and if a tertiary harmonic is existent, Q takes a value of 3.

After the correction, a distance E3 between the spectral position $peak'_{ppg1pos}$ of the second feature point and a second spectral position $peak_{acc1pos}$ of the maximum value point in the second feature point is determined.

After the correction, a bandwidth E4 of a statistical value of the spectral position $peak'_{ppg1pos}$ of the second feature point on the frequency-domain heart rate detection data is determined.

After the correction, an amplitude E5 of the second feature point is determined.

The greater the E1 and E2, the smaller the confidence value of the first feature point, and the smaller the E1 and E2, the greater the confidence value of the first feature point; the smaller the E3, the smaller the confidence value of the first feature point, and the greater the E3, the greater the confidence value of the first feature point; and the greater the E4 or the E5, the smaller the confidence value of the first feature point, and the smaller the E4 or the E5, the greater the confidence value of the first feature point. In this embodiment, the confidence value may be understood as representing the probability that the frequency-domain heart rate detection data may be finally used for the heart rate detection. A greater the confidence value indicates a great probability that the frequency-domain heart rate detection data may be used for the heart rate detection.

Further, assume that a maximum value of the confidence value is 100 and a minimum value of the confidence value is 0. With respect to each reserved second feature point, according to the values of E1, E2, E3, E4 and E5, the confidence values representing the confidence may be respectively defined as V1, V2, V3 and V4. In this case, each reserved second feature point has a confidence value of $$\text{Score}_{peak'_{ppg}}(n')=(V1+V2+V3+V4)/4.$$

Alternatively, by weighting averaging calculation according to the actual application environment, the weights of E1, E2, E3, E4 and E5 are respectively θ1, θ2, θ3, θ4 and θ5, and the confidence value is $$\text{Score}_{peak'_{ppg}}(n')=\theta_1*E1+\theta_2*E2+\theta_3*E3+\theta_4*E4+\theta_5*E5, \text{ where}$$

$$\theta1+\theta2+\theta3+\theta4=\theta5=1.$$

S509: The heart rate is calculated according to a frequency corresponding to the second feature point having a maximum confidence value if there is a second feature point whose confidence value is greater than a defined confidence threshold.

A frequency is predicted based on historical heart rate to calculate the heart rate based on the predicted frequency if there is no second feature point whose confidence value is greater than the defined confidence threshold. The confidence threshold may be specifically determined according to the accuracy of the heart rate detection. If a higher accuracy is required, the value of the confidence threshold is greater, and otherwise, the value of the confidence threshold is smaller.

If there is a second feature point whose confidence value $\text{Score}_{peak'_{ppg}}(n')$ is greater than the defined confidence threshold $Th_{conf}$, the spectral position (that is, the frequency value) corresponding to the second feature point whose confidence value is the maximum is used as the current heart rate $freq_{cur}$; or if there is no second feature point whose confidence value is greater than the defined confidence threshold, the current heart rate cur is $freq_{cur}$ is predicted based on the historical heart rate; and the heart rate $HB_{curtemp}$ is calculated based on the current heart $freq_{cur}$. The details may be referenced to formula (20).

$$HB_{curtemp}=(f1+\Delta f*\text{freq}_{cur})*60 \qquad (20)$$

In formula (20), $HB_{curtemp}$ represents the calculated heart rate, $freq_{cur}$ represents the current heart rate, denotations of f1 and $\Delta f$ may be referenced to the description of the curve Z transformation.

The heart rate $HB_{curtemp}$ is obtained by calculation based on the time-domain analysis and the frequency-domain analysis. However, the accuracy of the heart rate $HB_{curtemp}$ may be further improved. Accordingly, based on the above embodiment, a tracking and optimization process is further added. Specifically, the heart rate calculated based on the time-domain analysis and the frequency-domain analysis is tracked and optimized according to the historical heart rate and the feature data of the subject in motion. It should be noted that the tracking and optimization process may be executed by a computing module as illustrated in FIG. 1.

It should be noted that the above embodiments discloses the step of correcting the second feature point. However, where the second feature point does not need to be corrected, the above correction step may be omitted.

Figure 8:
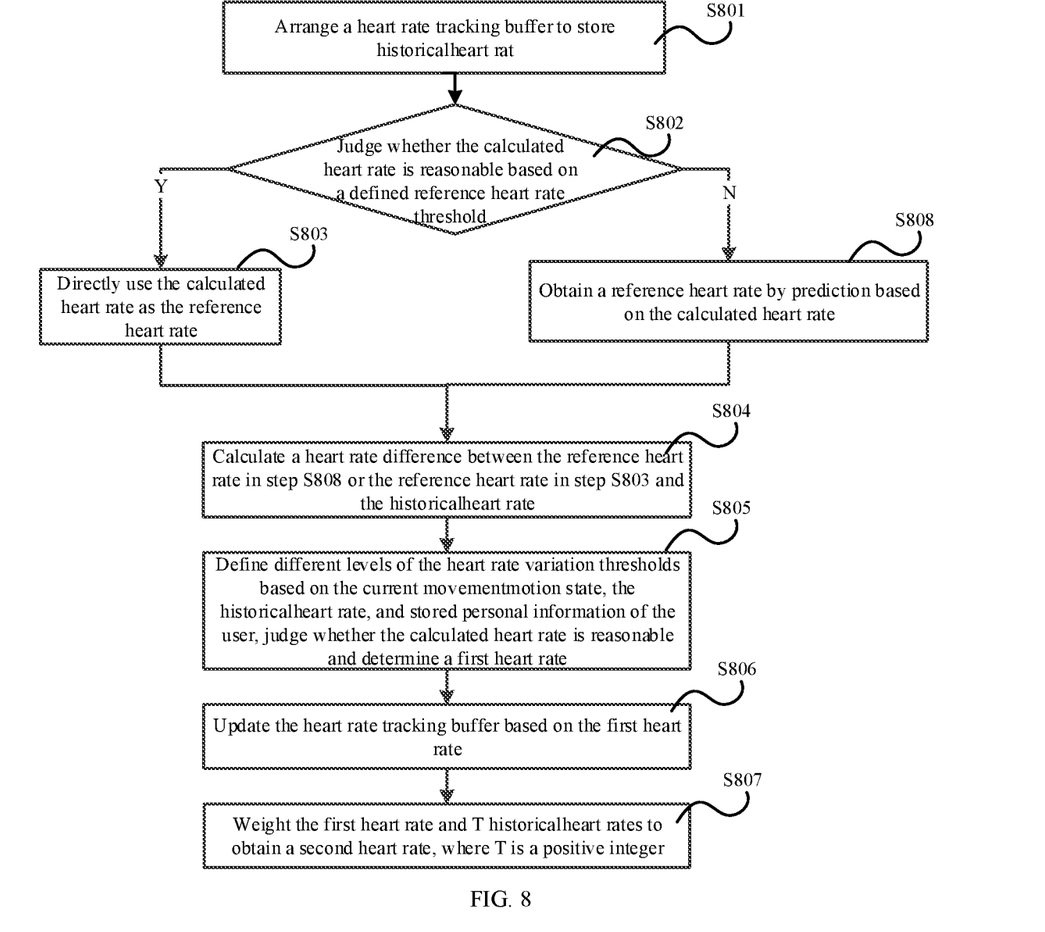
FIG. 8 is a schematic flowchart of tracking and optimization according to an eighth embodiment of the present application.

FIG. 8 is a schematic flowchart of tracking and optimization according to an eighth embodiment of the present application. As illustrated in FIG. 8, the tracking and optimization include the following steps:

S801: A heart rate tracking buffer is arranged to store a historical heart rate.

In this embodiment, the heart rate tracking buffer $HB_{temp}$ buffer for storing the heart rate is arranged. The $HB_{temp}$ buffer has a user-defined length, and needs to be reasonably adjusted according to the quality of the current time-domain heart rate detection data and the current motion state, to satisfy any one or combination of a heart rate output delay, a heart rate change response speed and heart rate output accuracy.

S802: Whether the calculated heart rate is reasonable is judged according to a defined reference heart rate threshold; if the heart rate is reasonable, step S803 is performed; and if the heart rate is unreasonable, step S808 is performed.

In this embodiment, the reference heart rate threshold includes a reference heart rate upper threshold $HBTH_{max}$ and a reference heart rate lower threshold $HBTH_{min}$, where the reference heart rate upper threshold $HBTH_{max}$ and the reference heart rate lower threshold $HBTH_{min}$ correspond to the motion state. For example, in case of a strenuous motion state, the reference heart rate upper threshold $HBTH_{max}$ and the reference heart rate lower threshold $HBTH_{min}$ are both greater.

In this embodiment, if the heart rate HBcurtemp is within the range of the the reference heart rate upper threshold $HBTH_{max}$ and the reference heart rate lower threshold $HBTH_{min}$, the heart rate is reasonable, and otherwise, the heart rate is unreasonable.

S808: A reference heart rate is obtained by predicting based on the calculated heart rate.

In this embodiment, the last value $HB_{temp}$ buffer(N) in the $HB_{temp}$ buffer may be extracted as the reference heart rate $HB_{temp}$, and in this step, the reference heart rate $HB_{temp}$ may also be referred to as a predicted heart rate.

S803: The calculated heart rate is directly used as the reference heart rate.

S804: A heart rate difference between the reference heart rate in step S808 or the reference heart rate in step S803 and the historical heart rate is calculated.

In this embodiment, the heart rate difference $Heartrate_{diff}$ is calculated according to formula (21), $Heartrate_{pre}$ represents the historical heart rate in formula (20), where the historical heart rate is an actual heart rate of the user before the heart rate $HB_{curtemp}$ is calculated.

$$Heartrate_{diff} = |HB_{temp} - Heartrate_{pre}| \quad (21)$$

S805: Different levels of the heart rate variation thresholds are defined according to the current motion state, the historical heart rate, and stored personal information of the user, whether the calculated heart rate is reasonable is judged, and a first heart rate is determined.

In a specific application scenario, assume that k heart rate variation thresholds are defined according to the current motion state, the historical heart rate, and the stored personal information of the user, which are respectively $HBdiff_{th_1}, \ldots HBdiff_{th_k}$, and are ranked as follows: $HBdiff_{th_1} < HBdiff_{th_2} \ldots < HBdiff_{th_k}$.

If the difference between the calculated heart rate $HB_{curtemp}$ and the historical heart rate is less than $HBdiff_{th_1}$, it indicates that the calculated heart rate $HB_{curtemp}$ is reasonable; if the difference between the calculated heart rate $HB_{curtemp}$ and the historical heart rate is greater than $HBdiff_{th_1}$ but less than $HBdiff_{th_2}$, it indicates that the calculated heart rate $HB_{curtemp}$ needs to be corrected. The correction may be based on formula (22).

$$HB'_{temp} = Heartrate_{pre} + \lambda 2(HB_{temp} - Heartrate_{pre}) \quad (22)$$

In formula (22), $Heartrate_{pre}$ represents the historical heart rate, $HB_{temp}$ represents the heart rate before the correction, $HB'_{temp}$ represents the corrected heart rate, that is, the first heart rate, and $\lambda 2$ represents a correction adjustment factor.

Analogously, if the difference between the heart rate $HB_{curtemp}$ and the historical heart rate is greater than $HBdiff_{th_k}$, it indicates that the heart rate $HB_{curtemp}$ is unreasonable, and a reasonable heart rate $HB_{curtemp}$ needs to be predicted. Specifically, the reasonable heart rate may be predicted based on an existent and reasonable heart rate $HB_{curtemp}$. For example, the reasonable heart rate may be predicted by establishing a model based on the existent historical heart rate $HB_{curtemp}$.

S806: The heart rate tracking buffer is updated based on the first heart rate.

In this embodiment, in the updated heart rate tracking buffer, $HB_{temp}$ buffer=[$HB_{temp}$ buffer(2:N), $HB'_{temp}$. N is the number of buffered heart rates.

S807: The first heart rate and T historical heart rates are weighted to obtain a second heart rate, where T is a positive integer.

In a specific application scenario, assume that there are T historical heart rates, then a weight coefficient vector include T elements, that is, the weighting coefficient vector is $w_T = \{w_1, w_2, \ldots, w_T\}$, and the elements in the weighting coefficient vector simulate the variation trend of the heart rate, as follows:

1. If the heart rate is proximate to the maximum heart rate of the user, the elements in $W_T$ are ranked in an ascending order.

2. If the motion of the current user is strenuous, and the historical heart rate changes quickly but is still far from the maximum heart rate of the user, the elements in $W_T$ are entirely arranged to be greater to reflect quick variation trends of heart rate.

3. If the user changes from a relatively strenuous motion state to a relative smooth motion state, the elements in $W_T$ are ranked in a descending order.

4. If the motion state of the user is relatively stable, the elements in $W_T$ are equal to each other.

In addition, deep learning and matching may be carried out according to the stored heart rate variation features of the user to define the values of the elements in $W_N$.

In this embodiment, an output second heart rate HB may be specifically calculated according to formula (23).

$$HB = \frac{\sum_{i=1}^{T} HB_{temp} \text{buffer}(i) * W_T(i)}{\sum_{i=1}^{T} W_T(i)} \quad (23)$$

In formula (23), $HB_{temp}$ buffer(i) represents the ith historical heart rate, that is, the second heart rate is calculated based on a weighted average value.

In the above embodiment, the heart rate detection apparatus may be based on the photoplethysmograph detection principle. The motion sensor may be an acceleration sensor.

An embodiment of the present application further provides an electronic terminal. The electronic terminal includes the heart rate detection apparatus in the above embodiment. The electronic terminal may be specifically a smart phone, a smart earphone, a smart bracelet or the like.

The above described apparatus embodiments are merely for illustration purpose only. The modules which are described as separate components may be physically separated or may be not physically separated, and the components which are illustrated as modules may be or may not be physical modules, that is, the components may be located in the same position or may be distributed into a plurality of network modules. A part or all of the modules may be selected according to the actual needs to achieve the objectives of the technical solutions of the embodiments. Persons of ordinary skill in the art may understand and implement the present invention without paying any creative effort.

According to the above embodiments of the present invention, a person skilled in the art may clearly understand that the embodiments of the present invention may be implemented by means of hardware or by means of software plus a necessary general hardware platform. Based on such understanding, portions of the technical solutions of the present invention that essentially contribute to the related art may be embodied in the form of a software product, the computer software product may be stored in a computer readable storage medium. The computer-readable storage medium includes any mechanism for storing or transferring information in a computer readable form. For example, the computer-readable medium includes a read-only memory (ROM), a random access memory (RAM), a disk storage medium, an optical storage medium, a flash storage medium, electricity, light, sound and other forms of propagation signals (for example, a carrier, an infrared signal, a digital signal and the like), and the like. The computer software product includes several instructions for instructing a computer device (which may be a personal computer, a server, or a network device) to perform all the embodiments or some parts of the embodiments.

Finally, it should be noted that the above embodiments are merely intended to describe the technical solutions of the embodiments of the present application, instead of limiting the present application. Although the present application is described in detail with reference to the above embodiments, persons of ordinary skill in the art should understand that various modifications may be made to the technical solutions described in the above embodiments or equivalent replacements may be made to some technical features thereof, without departing from the spirit and scope of the technical solutions of the embodiments of the present application.

A person skilled in the art shall understand that the embodiments may be described to illustrate methods, apparatuses (devices), or computer program products. Therefore, hardware embodiments, software embodiments, or hardware-plus-software embodiments may be used to illustrate the embodiments of the present application. In addition, the embodiments of the present application may further employ a computer program product which may be implemented by at least one non-transitory computer-readable storage medium with an executable program code stored thereon. The non-transitory computer-readable storage medium comprises but not limited to a disk memory, a CD-ROM, and an optical memory.

The embodiments of the present application are described based on the flowcharts and/or block diagrams of the method, apparatus (device), and computer program product according to the embodiments of the present application. It should be understood that each process and/or block in the flowcharts and/or block diagrams, and any combination of the processes and/or blocks in the flowcharts and/or block diagrams may be implemented using computer program instructions. These computer program instructions may be issued to a computer, a dedicated computer, an embedded processor, or processors of other programmable data processing device to generate a machine, which enables the computer or the processors of other programmable data processing devices to execute the instructions to implement an apparatus for implementing specific functions in at least one process in the flowcharts and/or at least one block in the block diagrams.

These computer program instructions may also be stored a non-transitory computer-readable memory capable of causing a computer or other programmable data processing devices to work in a specific mode, such that the instructions stored on the non-transitory computer-readable memory implement a product comprising an instruction apparatus, where the instruction apparatus implements specific functions in at least one process in the flowcharts and/or at least one block in the block diagrams.

These computer program instructions may also be stored on a computer or other programmable data processing devices, such that the computer or the other programmable data processing devices execute a series of operations or steps to implement processing of the computer. In this way, the instructions, when executed on the computer or the other programmable data processing devices, implement the specific functions in at least one process in the flowcharts and/or at least one block in the block diagrams.

What is claimed is:

1. A method for detecting a heart rate, comprising:
acquiring a plurality of time-domain heart rate detection data;
if the plurality of time-domain heart rate detection data comprises a weak interference signal, extracting a first feature point from the plurality of time-domain heart rate detection data, and collecting statistics on feature data of the first feature point to determine time-domain heart rate detection data used in calculating the heart rate;
if the plurality of time-domain heart rate detection data comprises a strong interference signal, transforming the plurality of time-domain heart rate detection data to a frequency domain to obtain a plurality of frequency-domain heart rate detection data, extracting a second feature point from the plurality of frequency-domain heart rate detection data, and collecting statistics on feature data of the second feature point to determine frequency-domain heart rate detection data used in calculating the heart rate; and calculating the heart rate based on the time-domain heart rate detection data or the frequency-domain heart rate detection data used in calculating the heart rate;

wherein the first feature point comprises peaks and valleys, the collecting statistics on feature data of the first feature point to determine time-domain heart rate detection data used in calculating the heart rate comprises:
  collecting statistics on amplitudes of a plurality of peaks and amplitudes of a plurality of valleys, to determine a plurality of adjacent peak-valley amplitude differences; and
  determining the time-domain heart rate detection data used in calculating the heart rate based on the plurality of adjacent peak-valley amplitude differences;

wherein the determining the time-domain heart rate detection data used in calculating the heart rate based on the plurality of adjacent peak-valley amplitude differences comprises:
  collecting statistics on an average value of N contiguous adjacent peak-valley amplitude differences, N being an odd number; and
  if a middle adjacent peak-valley amplitude difference is less than a product of the average value and an adjustment factor, determining that the time-domain heart rate detection data of the peaks corresponding to the middle adjacent peak-valley amplitude difference is not used in calculating the heart rate.

2. The method according to claim 1, wherein the collecting statistics on feature data of the first feature point to determine time-domain heart rate detection data used in calculating the heart rate further comprises: collecting statistics on time points of a plurality of peaks and a plurality of distances between adjacent peaks; and
  correspondingly, the calculating the heart rate based on the time-domain heart rate detection data used in calculating the heart rate comprises:
  calculating the heart rate based on the distances of the plurality of adjacent peak distances corresponding to the time-domain heart rate detection data used in calculating the heart rate and a distance threshold set based on historical heart rate.

3. The method according to claim 2, wherein the calculating the heart rate based on the plurality of adjacent peak distances corresponding to the time-domain heart rate detection data used in calculating the heart rate and a distance threshold set based on historical heart rate historical comprises:
  calculating a reference peak distance based on the historical heart rate and a sampling frequency;
  setting at least one of a first distance threshold and a second distance threshold based on the reference peak distance;
  calculating a peak distance average value based on the plurality of adjacent peak distances corresponding to the time-domain heart rate detection data used in calculating the heart rate and at least one of the first distance threshold and the second distance threshold; and
  calculating the heart rate based on the peak distance average value and the sampling frequency.

4. The method according to claim 1, further comprising: acquiring a plurality of frequency-domain motion data of a motion sensor, and extracting a third feature point from the plurality of frequency-domain motion data to correct the frequency-domain heart rate detection data corresponding to the second feature point based on the third feature point, the third feature point comprising a maximum value of the plurality of frequency-domain motion data;

wherein the extracting a second feature point from the plurality of frequency-domain motion data to correct the frequency-domain heart rate detection data corresponding to the second feature point based on the third feature point comprises:
  upon the correction, extracting the second feature point from the plurality of frequency-domain heart rate detection data to determine the frequency-domain heart rate detection data used in calculating the heart rate, the second feature point comprising a relative maximum value point of the plurality of frequency-domain heart rate detection data.

5. The method according to claim 4, wherein the correcting the frequency-domain heart rate detection data corresponding to the second feature point based on the third feature point comprises:
  determining the frequency-domain heart rate detection data used in correcting the heart rate detection data based on the third feature point and a set frequency-domain amplitude threshold; and
  correcting the frequency-domain heart rate detection data used in correcting the heart rate detection data based on a fitting model of interference fitting.

6. The method according to claim 4, wherein the determining the frequency-domain heart rate detection data used in calculating the heart rate comprises:
  determining the frequency-domain heart rate detection data used in calculating the heart rate based on a spectrum position of the second feature point and a spectrum position threshold set based on the historical heart rate.

7. The method according to claim 5, wherein the determining the frequency-domain heart rate detection data used in calculating the heart rate comprises:
  determining the frequency-domain heart rate detection data used in calculating the heart rate based on a spectrum position of the second feature point and a spectrum position threshold set based on the historical heart rate.

8. The method according to claim 6, wherein the calculating the heart rate based on the frequency-domain heart rate detection data used in calculating the heart rate comprises:
  assigning a confidence value to the second feature point of the frequency-domain heart rate detection data used in calculating the heart rate;
  calculating the heart rate based on a frequency corresponding to the second feature point having a maximum confidence value if there is a second feature point whose confidence value is greater than a defined confidence threshold; and
  predicting a frequency based on the historical heart rate to calculate the heart rate based on the frequency historical if no second feature point whose confidence value is greater than the defined confidence threshold.

9. The method according to claim 8, wherein the confidence value is calculated based on one or more of the following combinations:
  a distance between a spectrum position of the second feature point of the frequency-domain heart rate detection data used in calculating the heart rate, and a spectrum position of the historical heart rate in the frequency-domain heart rate detection data;

a distance between the spectrum position of the second feature point of the frequency-domain heart rate detection data used in calculating the heart rate, and a spectrum position of the third feature point;

a bandwidth feature of the second feature point of the frequency-domain heart rate detection data used in calculating the heart rate; and an amplitude of the second feature point of the frequency-domain heart rate detection data used in calculating the heart rate.

10. The method according to claim 1, further comprising: tracking and optimizing the calculated heart rate based on the historical heart rate and feature data of a subject in motion.

11. The method according to claim 10, wherein the tracking and optimizing the calculated heart rate based on the historical heart rate and feature data of a subject in motion comprises:

calculating a heart rate difference based on the calculated heart rate, the historical heart rate and a defined reference heart rate threshold;

calculating a first heart rate based on the heart rate difference and a defined heart rate variation threshold; and weighting the first heart rate and T historical heart rates to obtain a second heart rate, T being a positive integer.

12. The method according to claim 11, wherein the calculating a heart rate difference based on the calculated heart rate, the historical heart rate and a defined reference heart rate threshold comprises:

judging whether the calculated heart rate is reasonable based on the defined reference heart rate threshold;

determining a heart rate difference between the calculated heart rate and the historical heart rate if the calculated heart rate is reasonable; and predicting the calculated heart rate and determining a heart rate difference between the predicted heart rate and the historical heart rate if the calculated heart rate is unreasonable.

13. The method according to claim 11, wherein the reference heart rate threshold comprises an upper reference heart rate threshold and a lower reference heart rate threshold, the upper reference heart rate threshold and the lower reference heart rate threshold corresponding to a motion state of the subject in motion.

14. The method according to claim 11, wherein the calculating a first heart rate based on the heart rate difference and a set heart rate variation threshold comprises:

judging whether the calculated heart rate is reasonable based on the heart rate difference and the set heart rate variation threshold;

using the calculated heart rate as the first heart rate if the calculated heart rate is reasonable; and correcting the calculated heart rate and using the corrected heart rate as the first heart rate if the calculated heart rate is unreasonable.

15. The method according to claim 11, wherein the heart rate variation threshold is set based on one or a combination of the motion state of the subject in motion, the historical heart rate and a feature attribute of the subject in motion.

16. A heart rate detection apparatus, comprising:

an acquiring module, configured to acquire a plurality of time-domain heart rate detection data;

a time-domain module, configured to: if the plurality of time-domain heart rate detection data comprises a weak interference signal, extract a first feature point from the plurality of time-domain heart rate detection data, and collect statistics on feature data of the first feature point to determine time-domain heart rate detection data used in calculating a heart rate;

a frequency-domain module, configured to: if the plurality of time-domain heart rate detection data comprises a strong interference signal, transform the plurality of time-domain heart rate detection data to a frequency domain to obtain a plurality of frequency-domain heart rate detection data, extract a second feature point from the plurality of frequency-domain heart rate detection data, and collect statistics on feature data of the second feature point to determine frequency-domain heart rate detection data used in calculating the heart rate; and a calculating module, configured to calculate the heart rate based on the time-domain heart rate detection data or the frequency-domain heart rate detection data used in calculating the heart rate;

wherein the first feature point comprises peaks and valleys, in collecting statistics on feature data of the first feature point to determine time-domain heart rate detection data used in calculating the heart rate, the time-domain module is further configured to:

collect statistics on amplitudes of a plurality of peaks and amplitudes of a plurality of valleys, to determine a plurality of adjacent peak-valley amplitude differences; and determine the time-domain heart rate detection data used in calculating the heart rate based on the plurality of adjacent peak-valley amplitude differences;

in determining the time-domain heart rate detection data used in calculating the heart rate based on the plurality of adjacent peak-valley amplitude differences, the time-domain module is further configured to:

collect statistics on an average value of N contiguous adjacent peak-valley amplitude differences, N being an odd number; and if a middle adjacent peak-valley amplitude difference is less than a product of the average value and an adjustment factor, determine that the time-domain heart rate detection data of the peaks corresponding to the middle adjacent peak-valley amplitude difference is not used in calculating the heart rate.

17. An electronic terminal, comprising a heart rate detection apparatus wherein comprising:

an acquiring module, configured to acquire a plurality of time-domain heart rate detection data;

a time-domain module, configured to: if the plurality of time-domain heart rate detection data comprises a weak interference signal, extract a first feature point in the plurality of time-domain heart rate detection data, and collect statistics for feature data of the first feature point to determine time-domain heart rate detection data involved in heart rate calculation;

a frequency-domain module, configured to: if the plurality of time-domain heart rate detection data comprises a strong interference signal, transform the plurality of time-domain heart rate detection data to a frequency domain to obtain a plurality of frequency-domain heart rate detection data, extract a second feature point in the plurality of frequency-domain heart rate detection data, and collect statistics for feature data of the second feature point to determine frequency-domain heart rate detection data involved in the heart rate calculation; and a calculating module, configured to calculate the heart rate according to the time-domain heart rate detection data or the frequency-domain heart rate detection data involved in the heart rate calculation;

wherein the first feature point comprises peaks and valleys, in collecting statistics on feature data of the first feature point to determine time-domain heart rate detection data involved in heart rate calculation, the time-domain module is further configured to:

collect statistics on amplitudes of a plurality of peaks and amplitudes of a plurality of valleys, to determine a plurality of adjacent peak-valley amplitude differences; and determine the time-domain heart rate detection data used in calculating the heart rate based on the plurality of adjacent peak-valley amplitude differences;

in determining the time-domain heart rate detection data used in calculating the heart rate based on the plurality of adjacent peak-valley amplitude differences, the time-domain module is further configured to:

collect statistics on an average value of N contiguous adjacent peak-valley amplitude differences, N being an odd number; and if a middle adjacent peak-valley amplitude difference is less than a product of the average value and an adjustment factor, determine that the time-domain heart rate detection data of the peaks corresponding to the middle adjacent peak-valley amplitude difference is not used in calculating the heart rate.

\* \* \* \* \*